United States Patent [19]

McGrath et al.

[11] Patent Number: 5,101,037
[45] Date of Patent: Mar. 31, 1992

[54] BIS(MALEIMIDO) PHENOXY PHENYLPHOSPHINE OXIDE

[75] Inventors: James E. McGrath; Paul A. Wood, III, both of Blacksburg, Va.

[73] Assignee: Virginia Tech Intellectual Properties, Inc., Blacksburg, Va.

[21] Appl. No.: 750,361

[22] Filed: Aug. 27, 1991

[51] Int. Cl.$^5$ ............................................. C07F 9/02
[52] U.S. Cl. .................................................. 548/413
[58] Field of Search ........................................ 548/413

[56] References Cited

U.S. PATENT DOCUMENTS 4,276,344  6/1981  Varma et al. .................. 428/367
4,973,631  11/1990  McGrath et al. ................ 525/534

OTHER PUBLICATIONS

CA 111:39992k Synthesis of Polyimidazoles via Aromatic Nucleophilic Displacement, Connell et al., 1989, p. 9.
CA 93:8757t Thermostable Heterocyclic Polymers, Chernikhov et al., 1978, p. 18.

Primary Examiner—Mary C. Lee
Assistant Examiner—Joseph K. McKane
Attorney, Agent, or Firm—Richard P. Fennelly; Louis A. Morris

[57] ABSTRACT

Bis(maleimido) phenoxy phenylphosphine oxide monomers are formed by reacting a bis(aminophenoxyphenyl) phosphine oxide, e.g., bis(3-aminophenoxy) triphenylphosphine oxide, with maleic anhydride forming the intermediate bismaleamic acid species which is cyclodehydrated to the desired bismaleimido compound. The improved properties include: (1) a low melting point ($T_m = 90°$ C.); (2) a wide processing temperature range ($T_{cure} = 210°$ C.); and (3) a high $T_g$ value of 400° C.; and (4) a high char yield which suggests flame resistance.

8 Claims, No Drawings

BIS(MALEIMIDO) PHENOXY PHENYLPHOSPHINE OXIDE

BACKGROUND OF THE INVENTION

Bismaleimides are well known to be important thermosetting resin systems that have developed at a rapid rate during the last decade. Traditionally, epoxies have been the major resin chosen for advanced composites and adhesives. However, the limitation with epoxies is that their upper temperature range for structural performance is restricted to approximately 180° C. in dry and 110° C. in wet atmospheres. Higher temperature performance resins are needed for composites in applications where epoxies cannot be used, but unfortunately as high temperature properties are increased, the ease of processability of the resins is often reduced. Bismaleimides are preferred as matrix resins for composites over epoxies when high temperature resistance, good hot-wet environmental stability and improved fire, smoke and toxicity properties are required.

One of the advantages of most bismaleimide resins is their high glass transition temperature, which is required for many aerospace applications. The methylene dianiline based systems, although considered widely to be the work horse of the BMI industry have been found to be both extremely brittle and to undesirably contain quantities of the precursor carcinogenic methylene dianiline in the polymerization mixtures. This large degree of brittleness no doubt results from the high crosslink density due to the short bismaleimide segments, as well as crosslinks via the benzylene methylene unit. The brittle bismaleimide networks result in composites with microcracks and low damage tolerance. Bismaleimides derived from aromatic diamines are crystalline compounds with relatively high melting points. Unfortunately, the high melting temperature of the uncured bismaleimide results in a narrow processing window. Once the bismaleimide resin melts, it immediately begins to cure, making processing difficult for the neat resins. One means to overcome this drawback is to copolymerize the bismaleimide with molar deficiencies of comonomers such as diamines via the Michael addition reaction. Such chain extension improves the processability and reduces the melting point and the inherent brittleness of the bismaleimides. In practice, bismaleimides are prereacted with an aliphatic branched diamine to produce a lower melting of even liquid precursor, which has a wider thermal processing window relative to its flow behavior and network formation. It would be desirable to produce a somewhat tougher BMI system which would again cure without any volatiles eliminated that would be based upon less environmental hazardous, preferably single component precursors. It is also desirable to prepare systems that can liquefy at relatively low temperatures and possess an adequate processing window. Materials showing improved flame retardancy are also sought. These needs have led us to investigate new BMI chemistry.

A wide variety of bismaleimides have been prepared with the aim of tailoring specific resin properties by simply changing the structure and molecular weight of the diamine used for the synthesis. Some literature and patent disclosures considered relevant to the subject matter claimed herein are the following:

1. U.S. Pat. No. 4,276,344 to R. A. Forsch et al. illustrate bisimide formation using a phosphorus-containing aromatic diamine in which the bridging phosphorus moiety has the formula

where R is methyl, ethyl or phenyl; and

2. I. K. Varma et al., in J. Macromol. Sci-Chem., A19(2), pp. 209-224 (1983) show trisimide and bisimide monomers derived from tris(m-aminophenyl) phosphine oxide by reaction with the selected anhydride.

SUMMARY OF THE INVENTION

Novel bis((maleimido) phenoxy triphenyl)phosphine oxide monomers are the subject of the present invention.

DETAILED DESCRIPTION OF THE INVENTION

The diamine reagent used herein is a bis(aminophenoxyphenyl) phosphine oxide of the formula

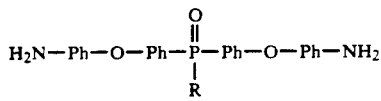

where Ph represents a phenyl group and R represents an alkyl (such as methyl or ethyl) or, preferably, an aryl group. The phenyl/aryl substituents are preferably unsubstituted and the amino substituents (—NH$_2$) are non-para in orientation although the present invention also contemplates having the amino substituents in the para-position as well. As will be noted from the foregoing structure, there are ether linkages in the diamine which should serve to increase the toughness of any resin made from the bismaleimides described herein.

The reaction of the above type of phosphine oxide-containing diamine with maleic anhydride in acetone using acetic anhydride and sodium acetate, while under nitrogen pressure, has been found suitable to prepare the intermediate bismaleamic acid phenoxy phenylphosphine oxide. This bismaleamic acid precipitates out of solution after a short period of time and can be readily cyclodehydrated to the desired bismaleimide using acetic anhydride and sodium acetate as the catalyst. The combination of acetic anhydride, sodium acetate and bismaleamic acid can be brought up to reflux temperature (about 60° C.) to yield a homogeneous solution which can be refluxed (e.g., for three hours) to yield the desired product. A description of this general synthetic route is given by D. Kumar in Chemistry and Industry, 21 March 1981, pp. 189-191.

The monomers formed in accordance with this invention show surprisingly low melting points, extended processing windows, high T$_g$ values and high char yields, the latter suggesting improved flame resistance.

Certain embodiments of this invention are described in the Examples which follow.

EXAMPLE

The intermediate bismaleamic acid was prepared by adding bis-4-[(3'-aminophenyl)phenyl]phenylphosphine oxide (0.2584 mole), maleic anhydride (0.6202 mole) and acetone (1200 ml) to a 2 L four-neck round bottom flask fitted with a nitrogen inlet, overhead mechanical stirrer, thermometer, and a water condenser. The yellow bismaleamic acid precipitated out of solution after five minutes at room temperature. The precipitated solution was stirred for an additional hour. The bismaleimide was then prepared in situ by adding acetic anhydride (1.6295 mole) and sodium acetate (0.1890 mole) and refluxing the reaction mixture. The mixture became homogeneous at reflux and was allowed to proceed for an additional three hours. The homogeneous, brown solution was then filtered and the filtrate was reduced in volume by using a rotary evaporator. The resulting two-thirds brown syrup was precipitated in water using a blender, and the precipitate was washed several times with water. The light tan bismaleimide solid was vacuum oven dried for forty-eight hours at 60° C. The yield was 95%.

The DSC scan for the uncured bis-4-[(3'-maleimidophenoxy)phenyl]phenylphosphine oxide indicated melting at around 90° C. ($T_m$) and an exotherm, indicating curing, which did not take place until more than 180° C. ($T_i$), with a peak exotherm noted at about 210° C. ($T_{exo}$). The cured material showed a very high glass transition temperature at about 400° C. as determined by TMA. DMTA showed the presence of a β-relaxation peak at about $-100°$ C. suggesting an improved fracture toughness relative to the methylene dianiline BMI materials which show no β-relaxation. Isothermal TGA scans at 300° C. for twelve hours showed no weight loss. Dynamic TGA scans of the cured maleimide showed it to be stable in air to 400° C. with a significant char yield that may be important in flame retardant systems. The cured material was resistant to flame ignition and propagation, and it had a low combustibility with a very low smoke emission. There appeared to be a wider processing window for this material (which is deemed useful as a structural adhesive or matrix resin) as compared to the methylene dianiline bismaleimide materials.

The foregoing Example has been presented for illustrative purposes only and should not, for that reason, be construed in a limiting sense. The scope of protection sought is set forth in the claims which follow.

We claim:

1. A bis((maleimido) phenoxy phenyl)phosphine oxide compound.

2. A compound as claimed in claim 1 having the formula

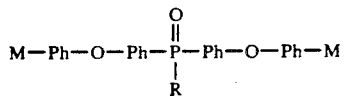

where M is a maleimido group, Ph is phenyl, and R is selected from the group consisting of alkyl and aryl.

3. A compound as claimed in claim 2 wherein R is aryl.

4. A compound as claimed in claim 2 wherein R is aryl and the groups M are 3-phenoxy in position 5. A compound as claimed in claim 2 wherein R is alkyl.

6. A compound as claimed in claim 2 wherein R is alkyl and the groups M are 3-phenoxy in position.

7. A compound as claimed in claim 5 wherein R is methyl.

8. A compound as claimed in claim 6 wherein R is methyl.

* * * * *